(12) United States Patent
Silva Guisasola et al.

(10) Patent No.: US 6,509,466 B2
(45) Date of Patent: Jan. 21, 2003

(54) PROCESS FOR OBTAINING 17 β-(N-TERT-BUTYLCARBAMOYL)-3-ONE-4-AZA-STEROIDS

(75) Inventors: Luis Octavio Silva Guisasola, Boecillo (ES); Cristina Blanco Fernandez, Boecillo (ES); Antonio Lorente Bonde-Larsen, Boecillo (ES); Jorge Martin Juarez, Boecillo (ES)

(73) Assignee: Raga Consultores, S.L., Boecillo (ES)

( * ) Notice: Subject to any disclaimer, the term of this patent is extended or adjusted under 35 U.S.C. 154(b) by 0 days.

(21) Appl. No.: 09/800,019

(22) Filed: Mar. 5, 2001

(65) Prior Publication Data

US 2001/0008895 A1 Jul. 19, 2001

Related U.S. Application Data

(63) Continuation of application No. PCT/ES00/00239, filed on Jul. 5, 2000.

(30) Foreign Application Priority Data

Jul. 5, 1999 (ES) ................................................ 9901487

(51) Int. Cl.[7] .............................................. C07D 221/18
(52) U.S. Cl. ........................................... 546/77; 546/61
(58) Field of Search ..................................... 546/77, 61

(56) References Cited

U.S. PATENT DOCUMENTS

| | | | |
|---|---|---|---|
| 4,760,071 A | 7/1988 | Rasmusson et al. | 519/284 |
| 5,670,643 A | 9/1997 | Davis et al. | 546/77 |

FOREIGN PATENT DOCUMENTS

| | | |
|---|---|---|
| EP | 0 367 502 A1 | 5/1990 |
| EP | 0 599 376 A2 | 6/1994 |
| EP | 0 655 458 A2 | 5/1995 |
| GB | 2 338 234 A | 12/1999 |
| WO | WO 95/00531 A1 | 1/1995 |

OTHER PUBLICATIONS

Peng Xia et al., "Synthesis of N–Substituted 3–Oxo–17β–Carboxamide–4–Aza–5α– Androstanes And The Tautomerism of 3–Oxo–4–Aza–5–Androstenes[1]", Heterocycles, vol. 47, No. 2, pp. 703–716, (1998).

*Primary Examiner*—Zinna Northington Davis
(74) *Attorney, Agent, or Firm*—Akin Gump Strauss Hauer & Feld, L.L.P.

(57) ABSTRACT

17β-(N-tert-butylcarbamoyl)-3-one-4-aza-steroids (I) can be obtained by a process which comprises the reaction of 17β-(alkoxycarbonyl)-3-one-4-aza-steroid with lithium tert-butylamide in an organic solvent. Some compounds of formula (I), for example, finasteride, are useful as inhibitors of 5α-reductase, and can be used in the treatment of benign prostatic hyperplasia and alopecia.

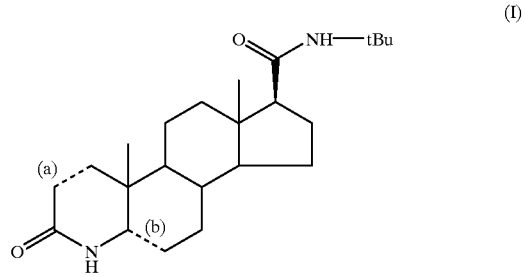

8 Claims, No Drawings

PROCESS FOR OBTAINING 17 β-(N-TERT-BUTYLCARBAMOYL)-3-ONE-4-AZA-STEROIDS

CROSS-REFERENCE TO RELATED APPLICATION

This application is a continuation of International Application No. PCT/ES00/00239 filed Jul. 5, 2000 the disclosure of which is incorporated herein by reference.

FIELD OF THE INVENTION

This invention relates to a process for obtaining 17β-(N-tert-butylcarbamoyl) -3-one-4-aza-steroids, optionally unsaturated between carbons 1–2 or 5–6, useful as inhibitors of 5α-reductase or synthetic intermediates thereof.

BACKGROUND OF THE INVENTION 4-aza-steroids are known that are useful as inhibitors of the enzyme 5α-reductase, an enzyme that converts testosterone into the more potent androgen, 5α-dihydro-testosterone, which is the main mediator of the androgenic activity in some organs. The inhibitors of testosterone-5α-reductase may prevent or reduce the symptoms of hyperandrogenic stimulation.

U.S. Pat. No. 4,760,071 describes some 17β-(N-alkylcarbamoyl)-4-aza-5α-androst-1-en-3-ones useful as inhibitors of 5α-reductase. A representative example of said compounds is finasteride [17β-(N-tert-butyl-carbamoyl)-4-aza-5α-androst-1-en-3-one], an active substance with multiple therapeutic applications, for example, in the treatment of benign prostatic hyperplasia and alopecia.

Known processes for obtaining 17β- (N-tert-butylcarbamoyl)-3-one-4-aza-steroids comprise the formation of a N-tert-butylcarbamoyl group.

The general processes for obtaining amides consist of reacting a derivative of carboxylic acid with the corresponding amine. The derivative of carboxylic acid may be an acid halide, an ester, a derivative of carbonyl or thionyl imidazole, a derivative of dicyclohexylcarbodiimide, etc.

When the derivative of carboxylic acid is an ester, its reaction with the amine to form the amide occurs satisfactorily when the ester and the amine have certain characteristics, such as high reactivity and absence of steric hindrance. When the structure of the ester and that of the amine are complex, the reactivity between both compounds reduces and the level of transformation may be practically zero. This occurs, for example, in the formation of 17β-(N-tert-butylcarbamoyl)-3-one-4-aza-steroids starting from 17β-(alkoxycarbonyl)-3-one-4-aza-steroids and tert-butylamine. In this case, said esters are not very reactive and the amine [tert-butylamine] presents a clear steric hindrance.

The solutions proposed in the state of the art for solving the problem of low reactivity between said esters and tert-butylamine may be sorted out in 3 groups:

a) those in which the amine is allowed to react with another derivative of carboxylic acid that confers on it greater reactivity, such as an acid halide; a representative example of this group is mentioned in U.S. Pat. No. 5,670,643, where the conversion of 17β-carboxy-4-aza-5α-androst-1-en-3-one into the corresponding acid chloride is described [see Example 1 of said U.S. Pat. No. 5,670,643]. This alternative, applied to an ester as a starting material, would imply the conversion of the ester into the acid and, subsequently, the conversion of the acid into the corresponding derivative, which would suppose the need of some additional synthetic steps that draw out the process and reduce the yield;

b) those in which the amine is activated by means of the formation of the corresponding derivative of magnesium-alkylamine by reacting the amine with a Grignard compound [see Examples 1 and 2 of the European patent application EP-A-0 655 458]. This alternative has the drawback that side reactions are produced by the presence of the Grignard compound in the reaction medium which may react with the ester group itself; and c) those which combine the conversion of the ester into a more reactive derivative and the activation of the amine, for example, the conversion of 17β-carboxy-4-aza-5α-androst-1-en-3-one into the corresponding derivative of imidazole and the conversion of the amine into the corresponding derivative of alkylaminomagnesium [see Example 5 of the patent application EP-A-0 367 502]. This alternative has the drawbacks of the alternatives a) and b).

The process of the present invention overcomes the whole or part of the drawbacks present in the processes of the state of the art.

DETAILED DESCRIPTION OF THE INVENTION

The invention provides a process for obtaining 17β-(N-tert-butylcarbamoyl)-3-one-4-aza-steroids of general formula (I)

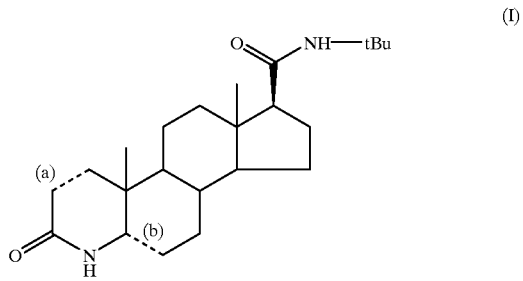

wherein each one of (a) and (b), independently, represents a single bond or a double bond, with the proviso that (a) and (b) are not simultaneously double bonds, which comprises reacting 17β-(alcoxycarbonyl)-3-one-4-aza-steroid of general formula (II)

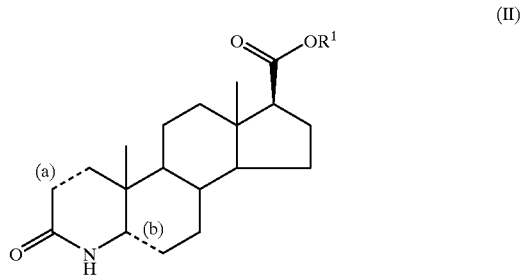

wherein (a) and (b) are those previously defined; and $R^1$ is an alkyl group of 1 to 3 carbon atoms; with lithium tertbutylamide in an organic solvent.

A preferred group of compounds of general formula (I) is that in which (a) represents a double bond, one of whose representative compounds is finasteride.

The compounds of general formula (II) are known compounds that can be obtained be means of processes described in the state of the art, for example, in U.S. Pat. No. 4,760,071.

Lithium tert-butylamide [tBuNHLi] may be easily obtained by reaction of tert-butylamine with butyllithium in an aprotic organic solvent, for example, tetrahydrofuran, according to the reaction:

tBuNH$_2$+BuLi - - -→tBuNHLi+BuH

In the sense used in this specification, the term "butyllithium" includes n-butyllithium, sec-butyllithium and terc-butyllithium.

The formation of lithium tert-butylamide takes place in a quantitative fashion, due to the strong basic character of butyllithium.

The reaction between the compound of formula (II) and lithium tert-butylamide is carried out in a molar ratio of at least 2 moles of lithium tert-butylamide per mole of compound of formula (II), in an aprotic organic solvent, such as an ether, for example, diethyl ether, di-isopropyl ether, dioxane or tetrahydrofuran, under an inert atmosphere, at a temperature comprised between −50° C. and 65° C. Once the reaction between the compound of formula (II) and lithium tert-butylamide has finished, the intermediate formed is hydrolysed, for example, with water, to give the compound of formula (I).

The reaction between the compound of formula (II) and lithium tert-butylamide seems to take place in accordance with the following scheme:

and R$^1$ have the previously defined meanings, is a novel compound and constitutes an additional object of this invention.

Similarly, the dilithiated derivative of 17β-(N-tert-butylcarbamoyl)-3-one-4-aza-steroid of general formula (IV), where (a) and (b) have the meanings defined previously, is a novel compound and constitutes an additional object of this invention.

Reaction between the compound of formula (II) and lithium tert-butylamide is a quick, selective reaction that takes place with a high yield. The high reactivity of the lithium tert-butylamide allows work at high concentrations with the subsequent saving in use of solvent.

The process of the invention presents numerous advantages, among which is found the reduction in the number of stages, an important aspect from the industrial point of view, as the conversion of the ester into another acid derivative is not required. Similarly, compared with the process comprising the activation of the amine by converting it into a derivative of tert-butylaminomagnesium, it has the following advantages:

greater reactivity of butyllithium compared to the Grignard reagent, for example, ethyl magnesium bromide, which implies a better transformation into the corresponding organo-metallic derivative of tert-butylamine without the coexistence in the reaction medium of butyllithium that would lead to side reactions;

it allows to work at higher concentrations, with the subsequent saving in use of solvent; and

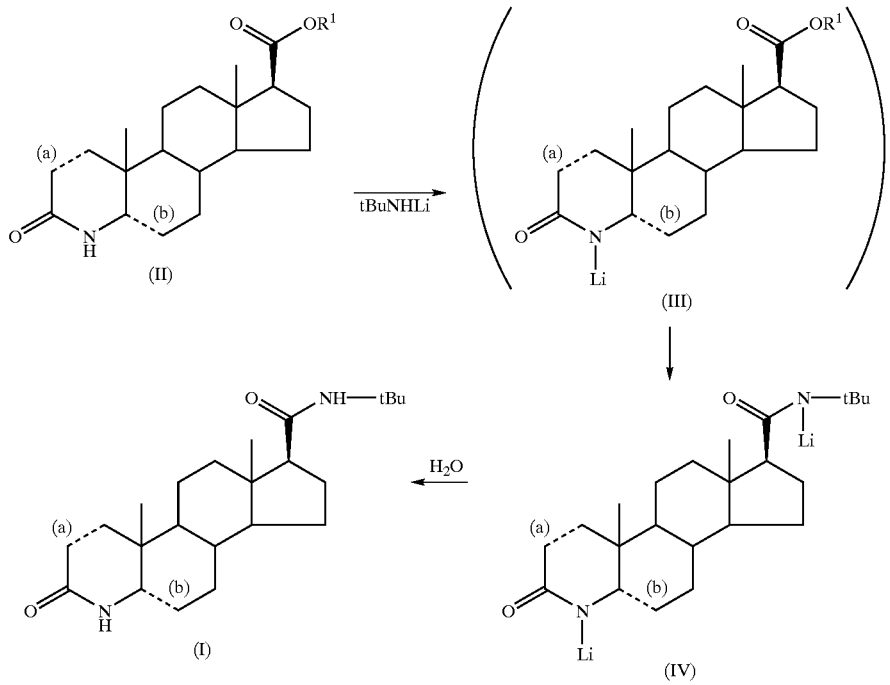

As can been seen from said scheme, a compound of formula (II) is converted into the dilithiated intermediate (IV), the hydrolysis of which yields the compound of formula (I). Although it is not desired to be linked by any theory, it seems that the dilithiated intermediate (IV) may be derived from the monolithiated intermediate (III).

The monolithiated derivative of 17β-(alkoxycarbonyl)-3-one-4-aza-steroid of general formula (III), where (a), (b)

the reaction of lithium tert-butylamide with the compound of formula (II) is practically quantitative.

Some compounds of formula (I), for example, finasteride, are inhibitors of 5α-reductase and may be used in the production of drugs for treatment of benign prostatic hyperplasia and alopecia.

The following examples illustrate the invention and should not be considered as limiting the scope thereof.

EXAMPLE 1

17β-(N-tert-butylcarbamoyl)-4-aza-5α-androstan-3-one

In a flask, preferable dry, under a nitrogen atmosphere, 29.9 ml of tert-butylamine (0.285 mol) are dissolved in 300 ml of dry THF and the solution is cooled to −50° C. Next, keeping the temperature below −40° C., 97.4 ml of 25% butyllithium in heptane (0.27 mol) are added. Once the addition is over, keeping the temperature below 40° C., 10 g (0,03 mol) of 17β-(methoxy-carbonyl)-4-aza-5α-androstan-3-one are added. The mixture is then heated under reflux, taking approximately 1 hour, and the reflux maintained for 4 hours. Once this period of time is up, it is checked that the reaction is complete and the mixture is cooled to below 0° C. Once this temperature is reached, 200 ml of water are added slowly, keeping the temperature below 5° C. Then, without letting the temperature exceed 20° C., concentrated hydrochloric acid is added until the pH is comprised between 3 and 3.5, and the solvents are removed under vacuum and the product is extracted with 100 ml of methylene chloride. The organic phase is washed 3 times with 50 ml of water and the organic solvent is removed under vacuum to give 11.2 g (99.7%) of 17β-(N-tert-butylcarbamoyl)-4-aza-5α-androstan-3-one which is recrystallised in ethyl acetate to give the title product with a melting point of 274–276° C.

EXAMPLE 2

17β-(N-tert-butylcarbamoyl)-4-aza-5α-androst-5-en-3-one 4.1 ml of tert-butylamine are dissolved in 12.7 ml of THF. The solution is made inert and cooled to below −20° C. Afterwards, 9.84 ml of 25% butyllithium in heptane are added. The resulting solution is added over 1 g [3.02 mmol] of 17β-(methoxycarbonyl)-4-aza-5α-androst-5-en-3-one suspended in 15.3 ml of THF. The reaction is carried out for 5 hours, gently heating the mixture until reflux is reached. The mixture is hydrolysed with water and the product is extracted with ethyl acetate to obtain 17β- (N-tert-butylcarbamoyl) -4-aza-5α-androst-5-en-3-one, with a yield of 76% (weight).

$^1$H NMR (300 MHz)δ 8.46 (s, 1H), 5.09 (s, 1H), 4.87–4.88 (m, 1H), 2.47–2.42 (m, 2H), 2.17–1.91 (m, 6H), 1.85–1.41 (m, 8H), 1.32 (s, 9H), 1.28–1.22 (m, 4H), 1.07 (s, 3H), 0.68 (s, 3H).

EXAMPLE 3

17β-(N-tert-butylcarbamoyl)-4-aza-5α-androst-1-en-3-one 8.18 ml of tert-butylamine are dissolved in 14 ml of THF, and the mixture made inert and cooled to below −40° C. Then, 30.9 ml of 2.5 M butyllithium in heptane are added. The resulting solution is added to 2 g [6.03 mmol] of 17β-(methoxycarbonyl)-4-aza-5α-androst-1-en-3-one suspended in 26 ml of THF. The reaction is allowed to proceed for 5 hours by slowly heating until reflux is reached. The mixture is hydrolysed with water and the product extracted with ethyl acetate to obtain 17β-(N-tert-butylcarbamoyl)-4-aza-5α-androst-1-en-3-one [mp: 252–254° C.], with a yield of 55% (by weight).

What is claimed is:

1. A process for obtaining a 17β-(N-tert-butylcarbamoyl)-3-one-4-aza-steroid of formula (I)

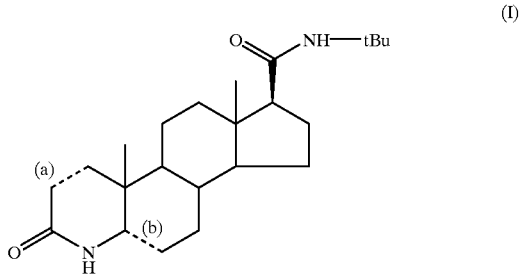

(I)

wherein each one of (a) and (b), independently, represents a single or a double bond, with the proviso that (a) and (b) are not simultaneously double bonds, comprising reacting 17β-(alkoxycarbonyl)-3-one-4-aza-steroid of formula (II)

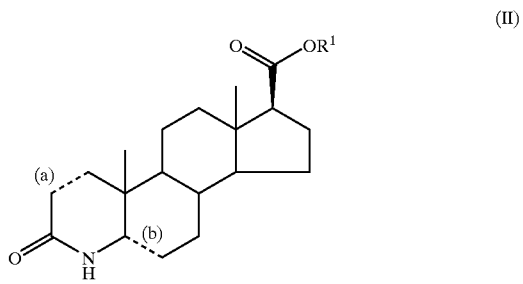

(II)

wherein (a) and (b) are as previously defined; and $R^1$ is an alkyl group of 1 to 3 carbon atoms; with lithium tert-butylamide in an organic solvent.

2. A process according to claim 1, wherein the molar ratio between the compound of formula (II) and lithium tert-butylamide is at least 2 moles of lithium tert-butylamide per mole of compound of formula (II).

3. A process according to claim 1, wherein said organic solvent is an aprotic organic solvent.

4. A process according to claim 1, wherein the reaction between the compound of formula (II) and lithium tert-butylamide is carried out at a temperature comprised between −50° C. and 65° C.

5. A process according to claim 1, wherein the reaction between the compound of formula (II) and lithium tert-butylamide is carried out under an inert atmosphere.

6. A process according to claim 1, wherein the compound obtained is 17β-(N-tert-butylcarbamoyl)-4-aza-5α-androst-1-en-3-one.

7. A monolithiated compound of 17β-(alkoxycarbonyl)-3-one-4-aza-steroid of formula (III)

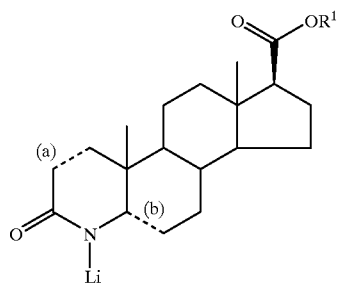

(III)

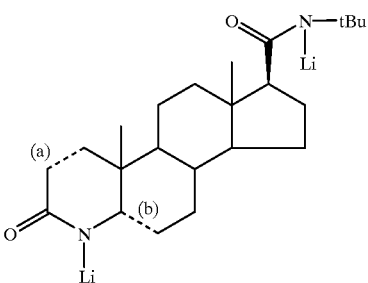

(IV)

wherein each one of (a) and (b), independently, represents a single bond or a double bond, with the proviso that (a) and (b) are not simultaneously double bonds, and $R^1$ is an alkyl group of 1 to 3 carbon atoms.

8. A dilithiated compound of 17β-(N-tert-butylcarbamoyl)-3-one-4-aza-steroid of formula (IV)

wherein each one of (a) and (b), independently, represents a single bond or a double bond, with the proviso that (a) and (b) are not simultaneously double bonds.

* * * * *